(12) United States Patent
Taheri et al.

(10) Patent No.: US 6,435,190 B1
(45) Date of Patent: Aug. 20, 2002

(54) AUTOGENOUS CELL PATCH CARDIO MYOPLASTY AND ADVANCED MUSCLE GRAFT IMPLANTATION SYSTEM

(76) Inventors: Syde A. Taheri, 1275 Delaware Ave., Buffalo, NY (US) 14209; Howard J. Leonhardt, 2400 N. Commerce Pkwy., Suite 408, Weston, FL (US) 33326

( * ) Notice: Subject to any disclaimer, the term of this patent is extended or adjusted under 35 U.S.C. 154(b) by 0 days.

(21) Appl. No.: 09/593,783

(22) Filed: Jun. 14, 2000

(51) Int. Cl.⁷ .............................................. A61B 19/00
(52) U.S. Cl. ....................................................... 128/898
(58) Field of Search ...................... 128/898; 623/14.13, 623/902; 600/37; 604/48, 264

(56) References Cited

U.S. PATENT DOCUMENTS

| | | | |
|---|---|---|---|
| 4,778,787 A | | 10/1988 | Castimpoolas ................ 514/25 |
| 5,223,400 A | * | 6/1993 | Ling et al. .................. 435/7.93 |
| 5,327,913 A | | 7/1994 | Taheri ......................... 128/898 |
| 5,458,582 A | * | 10/1995 | Nakao ......................... 604/528 |
| 5,516,533 A | * | 5/1996 | Badylak et al. ........... 623/14.13 |
| 5,591,183 A | * | 1/1997 | Chin ............................ 606/159 |
| 6,027,512 A | * | 2/2000 | Bridges ........................ 606/36 |
| 6,607,988 A | * | 5/2000 | Mueller ........................ 128/898 |

* cited by examiner

*Primary Examiner*—Corrine McDermott
*Assistant Examiner*—Thomas Barrett
(74) *Attorney, Agent, or Firm*—Walter W. Duft

(57) ABSTRACT

A method of autogenous cell patch cardio myoplasty using noninvasive thoracoscopy is disclosed. A patient's greater omentum is separated from its point of attachment to either the greater curvature of the stomach or the transverse colon. All open blood vessels in the greater omentum are ligated to permanently arrest bleeding. The greater omentum is introduced into the left pleural cavity through an opening in the diaphragm. Muscle grafts are removed from skeletal muscle tissue of the patient and an opening is formed in the pericardium to expose an area of damaged myocardium. Following attachment of the skeletal muscle grafts to either the greater omentum or the damaged myocardium area, preferably using an advanced muscle graft implantation system, the greater omentum is wrapped around the heart and attached thereto in order to reinforce the muscle grafts and enrich them with blood flow from the greater omentum.

11 Claims, 11 Drawing Sheets

AUTOGENOUS CELL PATCH CARDIO MYOPLASTY AND ADVANCED MUSCLE GRAFT IMPLANTATION SYSTEM

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention relates to cardio myopathy and the treatment thereof.

2. Description of the Prior Art

By way of background, cardio myopathy, as caused for example by myocardial infarction, is a common disorder. Twenty thousand new cases are reported yearly in the United States and 25–50% of such cases will result in death after three years. The problem is that damaged adult heart muscle does not regenerate and myocardial functionality cannot be restored using the body's natural healing mechanisms. The myocardium tends to dilate and areas of the ventricular walls may become hypokinetic, or even akinetic, such that congestive heart failure often develops in affected individuals.

Previous medical techniques have not substantially reduced the morbidity or mortality of this condition. Staged latissimus dorsi cardiomyoplasty is one mode of treatment. According to this method, latissimus dorsi muscle is pulled into the left pleural cavity and sutured to the damaged area. A disadvantage of this treatment is that eight weeks of muscle conditioning is required before the latissimus dorsi muscle is ready for attachment to the myocardium, and at least two operations are needed. A further proposal has also been made for an alternative treatment that involves the implantation of skeletal myoblasts, fetal cardiocytes or transformed embryonic stem cells into an infarcted myocardium. Laboratory research suggests that the implanted cells tend to fuse with surrounding muscle fibers to regenerate functional muscle that improves myocardial performance. This treatment, however, has not been clinically validated and it may be questioned whether the treatment can be effective without a mechanism for promoting new vascularization in and around the cell growth area.

More recently, one of the inventors herein patented a novel cardio myoplasty method involving use of an existing blood supplier, such as a patient's greater omentum, to provide support for, and deliver blood to, transplanted autogenous muscle grafts on an area of damaged tissue, such as the myocardium. See U.S. Pat. No. 5,327,913. This patent also discloses a novel instrument for retrieving muscle grafts from autogenous skeletal muscle tissue. What the patent does not disclose, however, is a system or method for attaching muscle grafts in place prior to applying the blood supplier. Accordingly, a need exists for an improved cardio myoplasty method and a related system providing a mechanism for muscle graft attachment.

SUMMARY OF THE INVENTION

The foregoing problems are solved and an advance in the art is obtained by an improved method of autogenous cell patch cardio myoplasty. Preferably using noninvasive thoracoscopy, autogenous muscle grafts are secured and then supported by the greater omentum to reinforce the dilated myocardium and correct diskinetic myocardium malfunction. In accordance with preferred embodiments of the invention, a patient's greater omentum is separated at or near its point of attachment to either the greater curvature of the stomach or the transverse colon. All open blood vessels in the greater omentum are ligated to permanently arrest bleeding. A free end of the greater omentum is then introduced into the left pleural cavity through an opening made in the diaphragm. Muscle grafts are removed from autogenous skeletal muscle tissue and an opening is formed in the pericardium to expose a damaged area of the myocardium. Following attachment of the skeletal muscle grafts to either the greater omentum or the damaged myocardium area, which is preferably performed using an advanced muscle graft implantation system, the greater omentum is wrapped around the heart and secured thereto in order to reinforce the muscle grafts and enrich them with blood flow.

BRIEF DESCRIPTION OF THE DRAWING

The foregoing and other features and advantages of the invention will be apparent from the following more particular description of preferred embodiments of the invention, as illustrated in the accompanying Drawing, in which.

DETAILED DESCRIPTION OF THE PREFERRED EMBODIMENT

Figure 1:
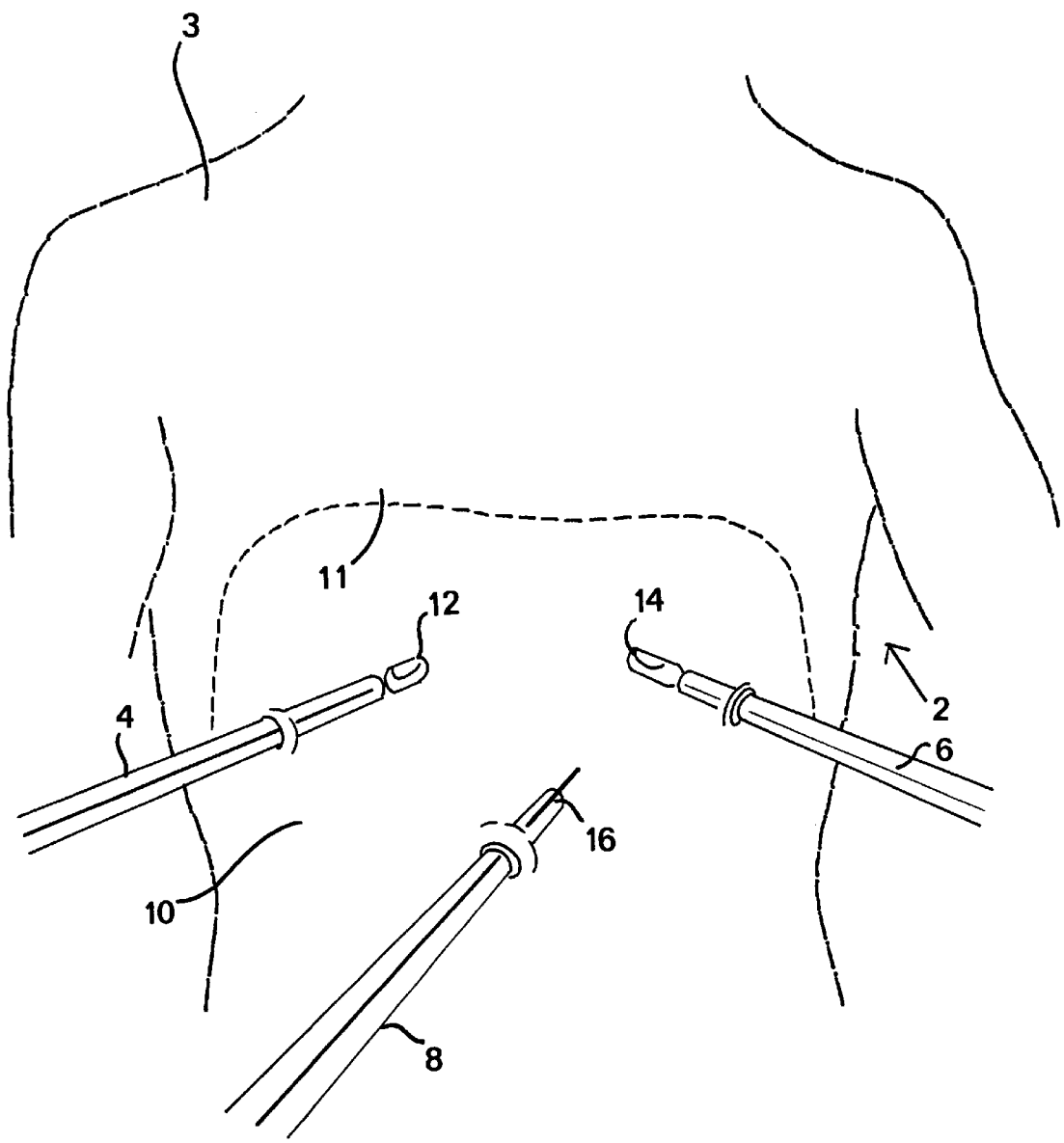
FIG. 1 is a plan view of a human torso showing the introduction of thoracoscopic instruments into a patient's trans-abdominal cavity in accordance with the invention.

Turning now to the figures, wherein like reference numerals represent like elements in all of the several views, FIG. 1 illustrates the torso 2 of a patient 3 who requires autogenous cell patch cardio myoplasty in accordance with the invention. To begin the procedure, three thoracoscopy ports 4, 6 and 8 are introduced into the patient's trans-abdominal cavity 10 (below the diaphragm 11) through openings previously made by trocars (not shown) in accordance with conventional thoroscoscopic techniques. Following conventional $CO_2$ insufflation, the ports 4 and 6 are respectively equipped with forceps 12 and 14, and the port 8 is equipped with a video camera 16.

Figure 2:
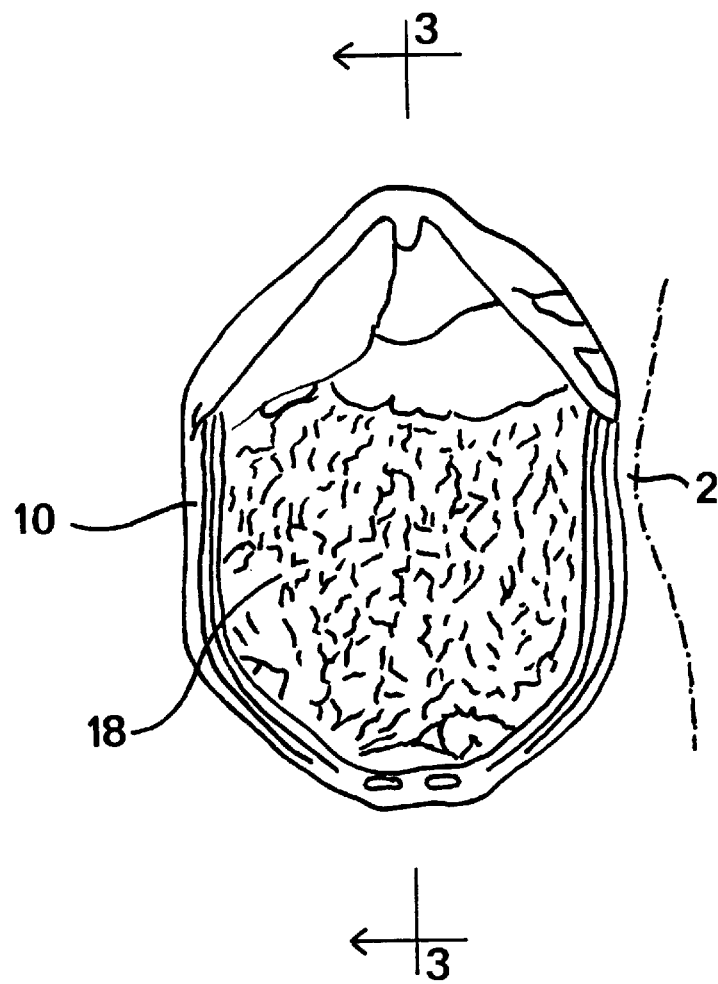
FIG. 2 is a plan view of a human torso with interior portions of the transabdominal cavity exposed to show the greater omentum in its normal position.
Figure 3:
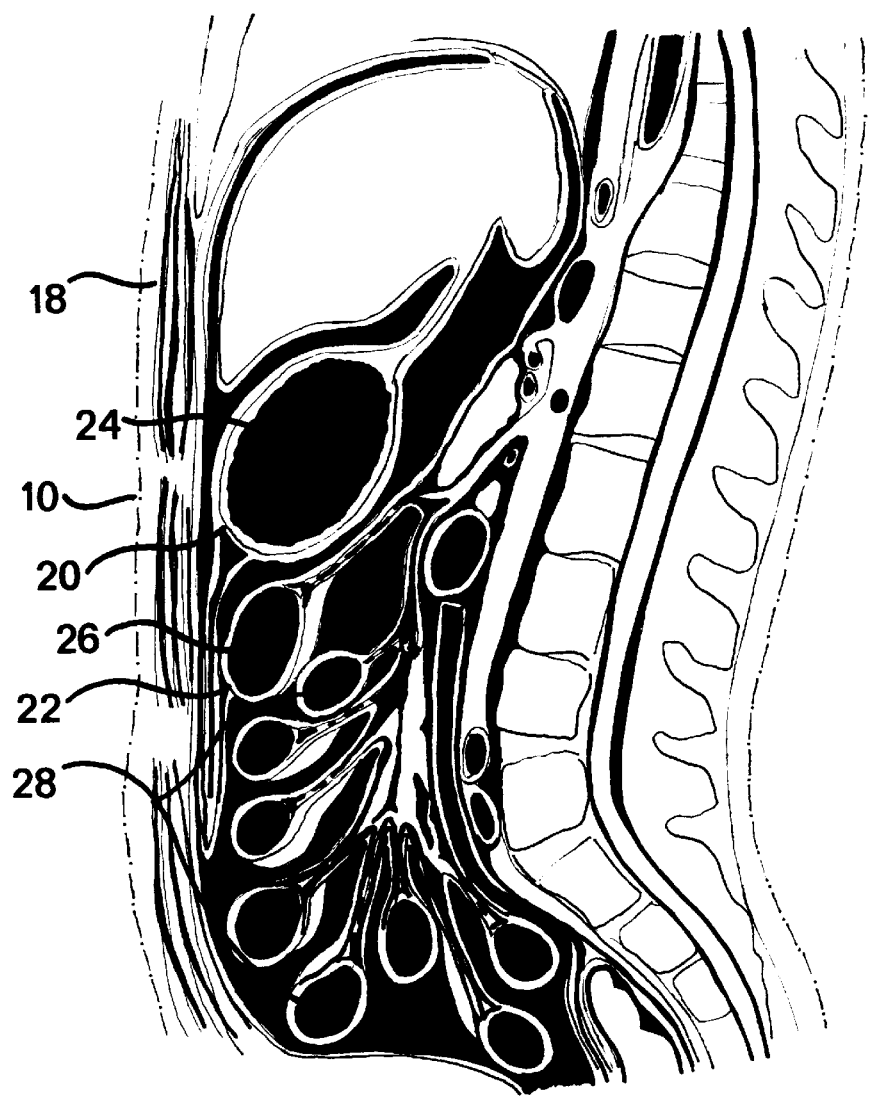
FIG. 3 is a cross-sectional view taken along line 3—3 in FIG. 2.

The initial phase of the cardio myoplasty procedure described herein is to locate the patient's greater omentum and tailor it to reach the myocardium through the left pleural cavity. In a first method step, the greater omentum is manipulated using the forceps 12 and 14 from its normal position to a raised position that allows the greater omentum to be dissected at or near its point of attachment to either the greater curvature of the stomach or the transverse colon. FIGS. 2 and 3 illustrate the interior of the patient's trans-abdominal cavity 10, and show the greater omentum 18 in its normal position. Reference numerals 20 and 22 of FIG. 3 respectively illustrate the locations where the greater omentum 18 is attached to the greater curvature of the stomach 24 and the transverse colon 26. For reference, the portions of the small intestine are shown by reference numeral 28.

Figure 4:
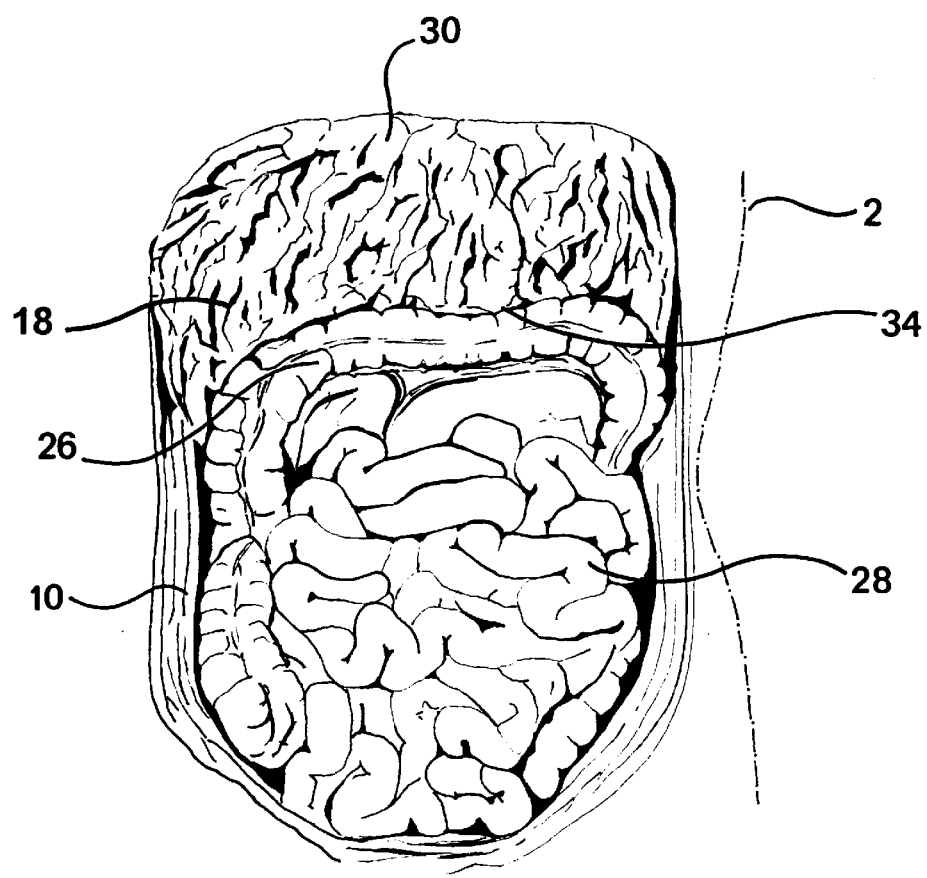
FIG. 4 is a plan view of a human torso with interior portions of the trans-abdominal cavity exposed to show the greater omentum after it has been manipulated into position for dissection.
Figure 5:
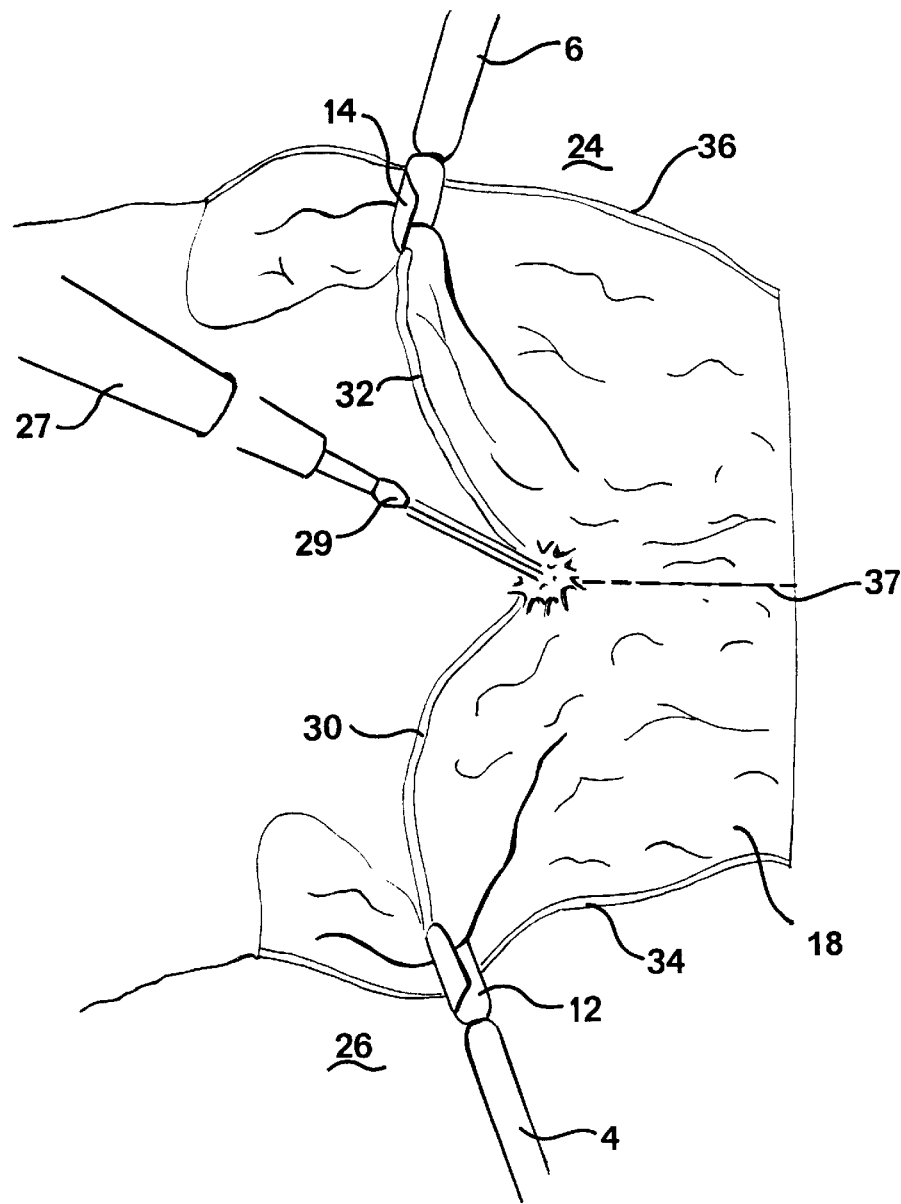
FIG. 5 is a plan view of a the greater omentum during dissection thereof.

FIG. 4 illustrates the greater omentum 18 prior to dissection thereof, with the greater omentum raised so that it can be dissected. FIG. 5 illustrates the dissection of the greater omentum 18. The greater omentum 18 can be dissected by laser or cautery scissors. One of the forceps 12 or 14 can be used to hold the greater omentum 18 during this procedure. The other can be removed and replaced with a laser or cautery scissors to perform the dissection. Alternatively, a fourth port could be used to carry the laser or cautery scissors in the event that both of the forceps 12 or 14 are required to manipulate the greater omentum 18 during dissection. By way of example only, FIG. 5 illustrates the use of a fourth port 27 carrying a laser 29 to perform the dissection.

Following dissection, the greater omentum 18 will have two free ends 30 and 32, and two corresponding base ends 34 and 36 respectively attached to, and receiving a supply of blood from, the transverse colon 26 and the greater curvature of the stomach 24. The dissection cut is shown by the dashed line 37 in FIG. 5. Because a free end of the greater omentum 18 must be able to reach the heart from a corresponding base end of the greater omentum, the dissection cut 37 is preferably made relatively close to either the greater curvature of the stomach 24 or the transverse colon 26. Insofar as the dissection step is performed using a laser or cautery scissors, any blood vessels of the greater omentum 18 that are opened as the dissection cut 37 is made will be ligated. In addition, if there are any other bleeding points remaining at this stage of the procedure, they are also ligated using conventional techniques.

Figure 6:
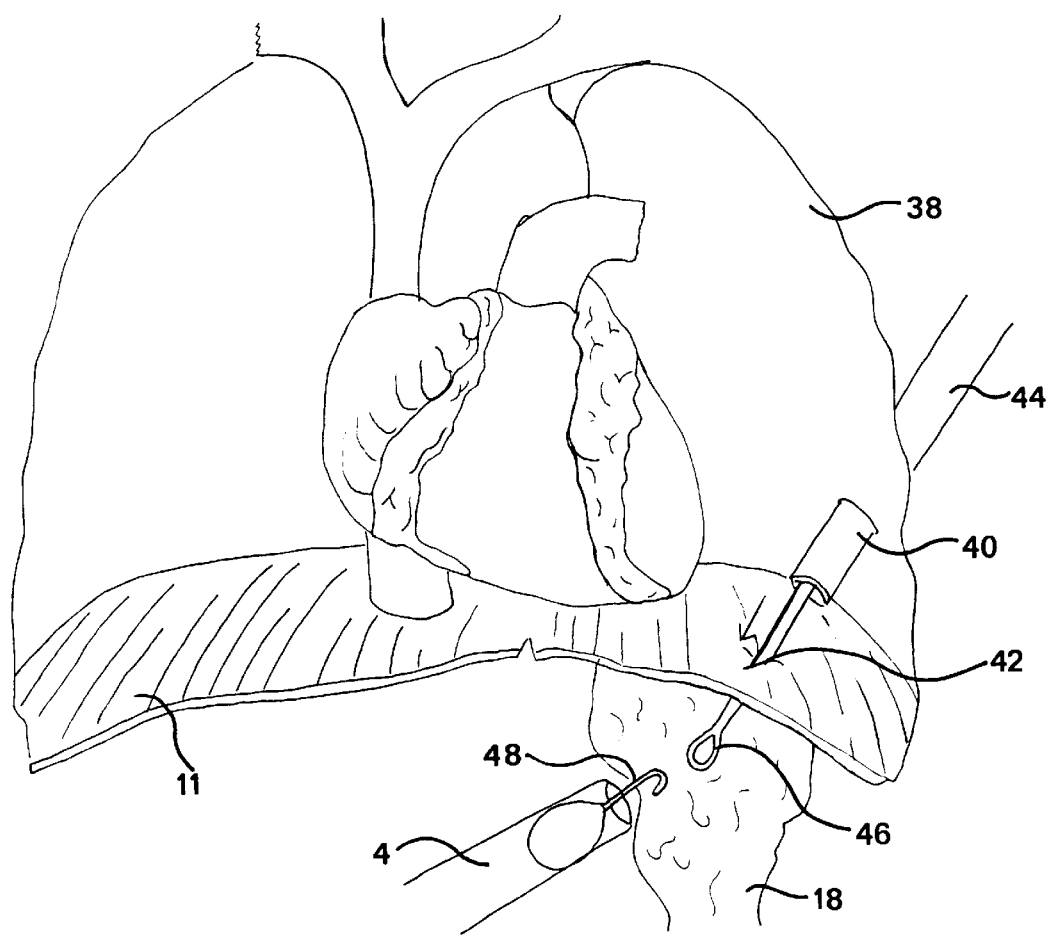
FIG. 6 is a plan view of a human torso with interior portions of the left pleural cavity exposed to show the penetration of the diaphragm to retrieve a free end of the greater omentum.

Turning now to FIG. 6, a second step of the cardio myoplasty procedure described herein is shown in which the diaphragm 11 is penetrated at 40 to retrieve one of the free ends 30/32 of the greater omentum 18 from the trans-abdominal cavity 10 into the left pleural cavity 38. More particularly, a trocar (not shown) is used to make an opening 40 between the left fifth or seventh intercostal space into the left pleural cavity 38, and to puncture the diaphragm 11 to form an opening 42. Following puncture of the diaphragm 11, the opening 42 is dilated to receive the greater omentum 18. Then a thoracoscopy port 44 having a forceps 46 is used to grasp the greater omentum 18 and pull it through the dilated opening 42 into the left pleural cavity 38. This can be assisted by a holding attachment 48 mounted to one of the thoracoscopy ports 4 or 6.

Figure 7:
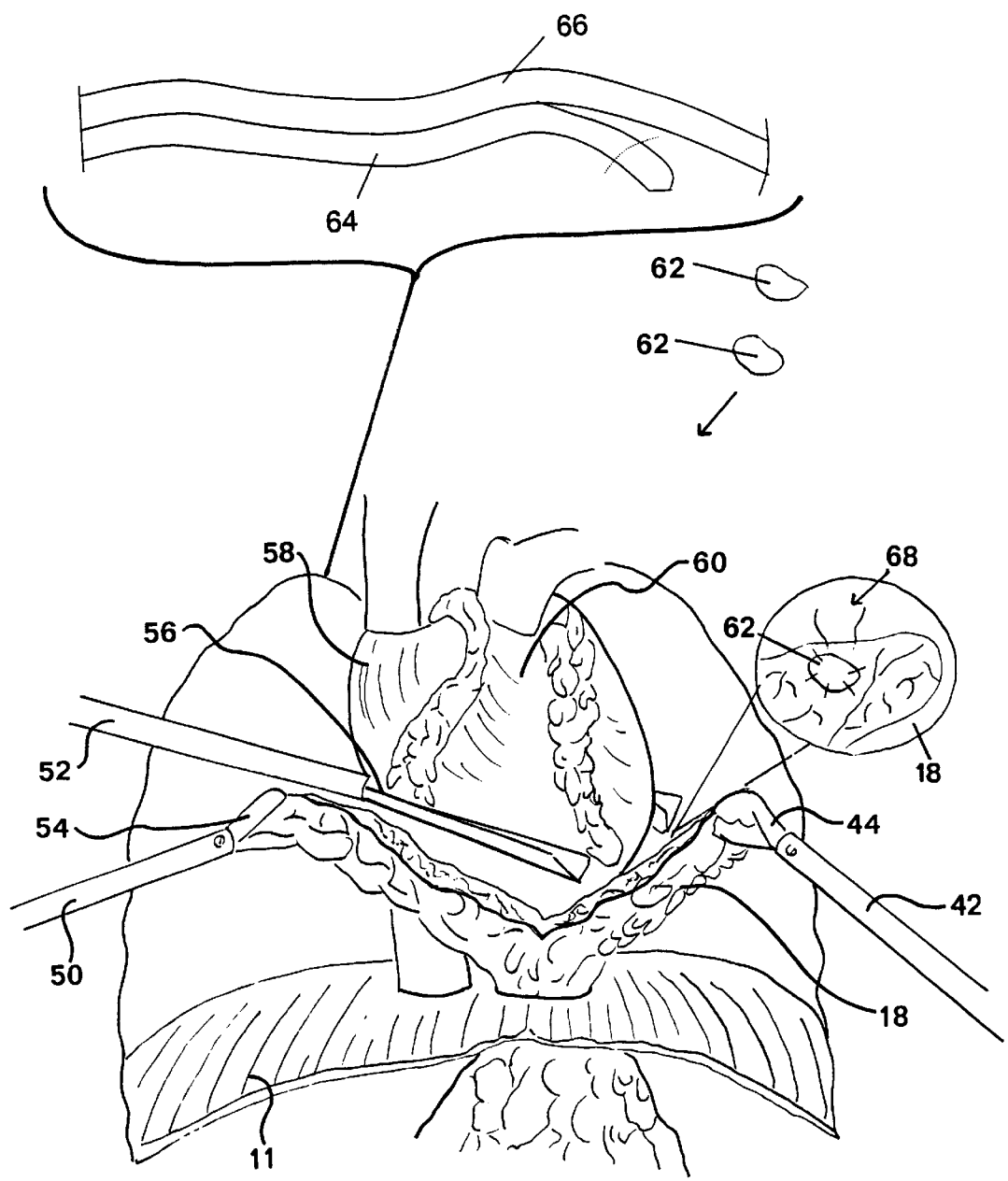
FIG. 7 is a plan view of a human torso with interior portions of the left pleural cavity exposed to show the greater omentum being spread apart by forceps around the heart, and further showing the sectioning of skeletal muscle from the chest wall and the securing of muscle grafts to the greater omentum.

FIG. 7 illustrates a third step in the cardio myoplasty procedure described herein in which a free end of the greater omentum 18 is spread by forceps, and in which autogenous skeletal muscle that has been sectioned from the patient is used to form an autogenous patch graft. More particularly, thoracoscopy ports 50 and 52 are introduced into the left pleural cavity 38 through openings (not shown) previously made by trocars (not shown). A forceps 54 is mounted to the thoracoscopy port 50 and a suitable manipulation tool 56 is mounted to an optional thoracoscopy port 52 for manipulating the position of the heart 58. Although not shown, a video camera is also introduced into the left pleural cavity 38 at the end of another thoracoscopy port.

Figure 8:
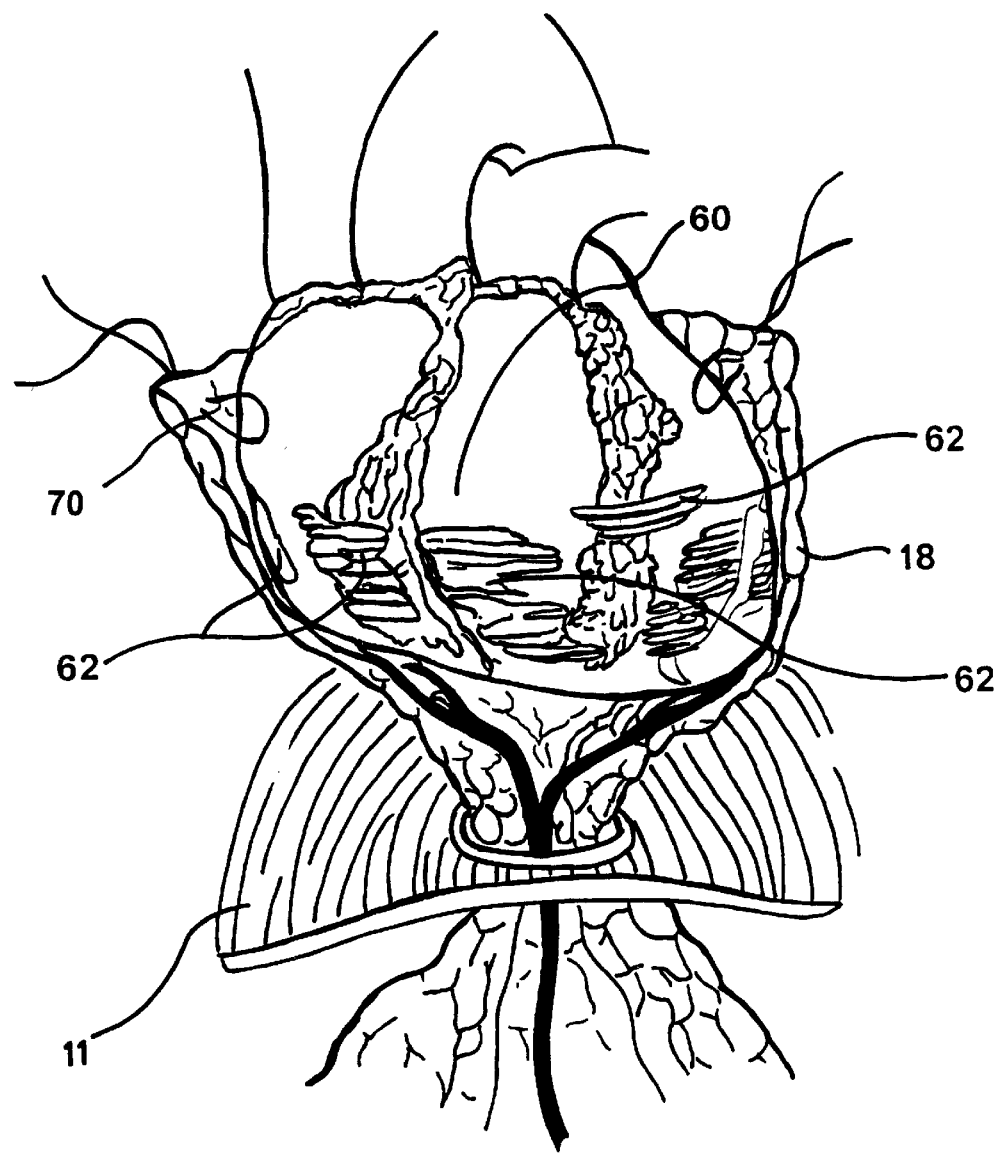
FIG. 8 is a plan view of the interior of the left pleural cavity showing the greater omentum being secured to the myocardium in an embodiment wherein muscle grafts are secured to the myocardium rather than the greater omentum.

Following introduction of a free end of the greater omentum 18 into the left pleural cavity 18, the pericardium (not shown) is incised to expose an area of the myocardium 60 that is damaged. Muscle grafts 62 are then removed from any suitable area where striated autogenous skeletal muscle tissue 64 can be found, such as the chest 66. If removed using a scalpel, each graft 62 will typically measure approximately 2.5×1.5 cm. Each graft can be attached using stapling, or by suturing (see reference numeral 68 in FIG. 7) to the greater omentum 18. Alternatively, as shown in FIG. 8, the muscle grafts 62 may be attached by stapling or suturing to the myocardium 60.

Figure 9:
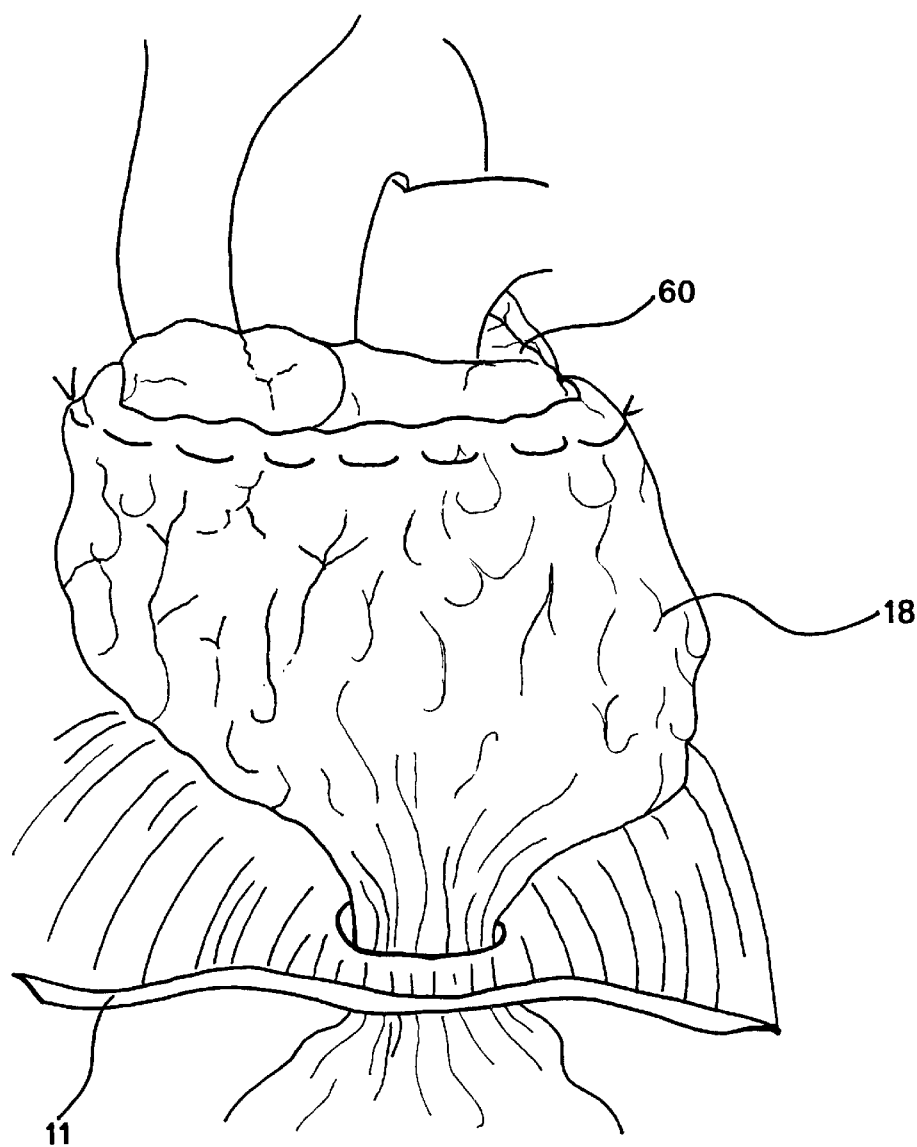
FIG. 9 is a plan view of the interior of the left pleural cavity showing the full attachment of the greater omentum to the myocardium.

Following attachment of the skeletal muscle grafts 62 to either the greater omentum 18 or the myocardium 60, a fourth and final step is performed in which the greater omentum is wrapped around all or a portion of the heart 58 and secured thereto. This places the greater omentum 18 in a contacting position to reinforce the muscle grafts 62 and enrich them with blood flow. FIG. 8 shows the divided greater omentum 18 being sutured to the myocardium at 70. Staples could also be used. FIG. 9 shows the completion of suturing of the greater omentum 18 to the myocardium 60 to support the autogenous cardiomyoplasty cell patch. The greater omentum 18 may then be tailored and sutured to the pericardium as necessary to fully enclose the damaged area of the myocardium 60.

The transplanted muscle tissue will now receive blood supply from the greater omentum 18, which remains attached to either the greater curvature of the stomach 24 or the transverse colon 26. If desired, the greater omentum 18 may now be used as a pathway for delivering a drug or medicine to the myocardium to speed recovery or to achieve other benefits. By way of example, a pocket (not shown) may be formed in the greater omentum to receive a delivery vehicle, such as a time-release capsule, containing the substance to be carried by the blood flow in the greater omentum to the myocardium.

Figure 10:
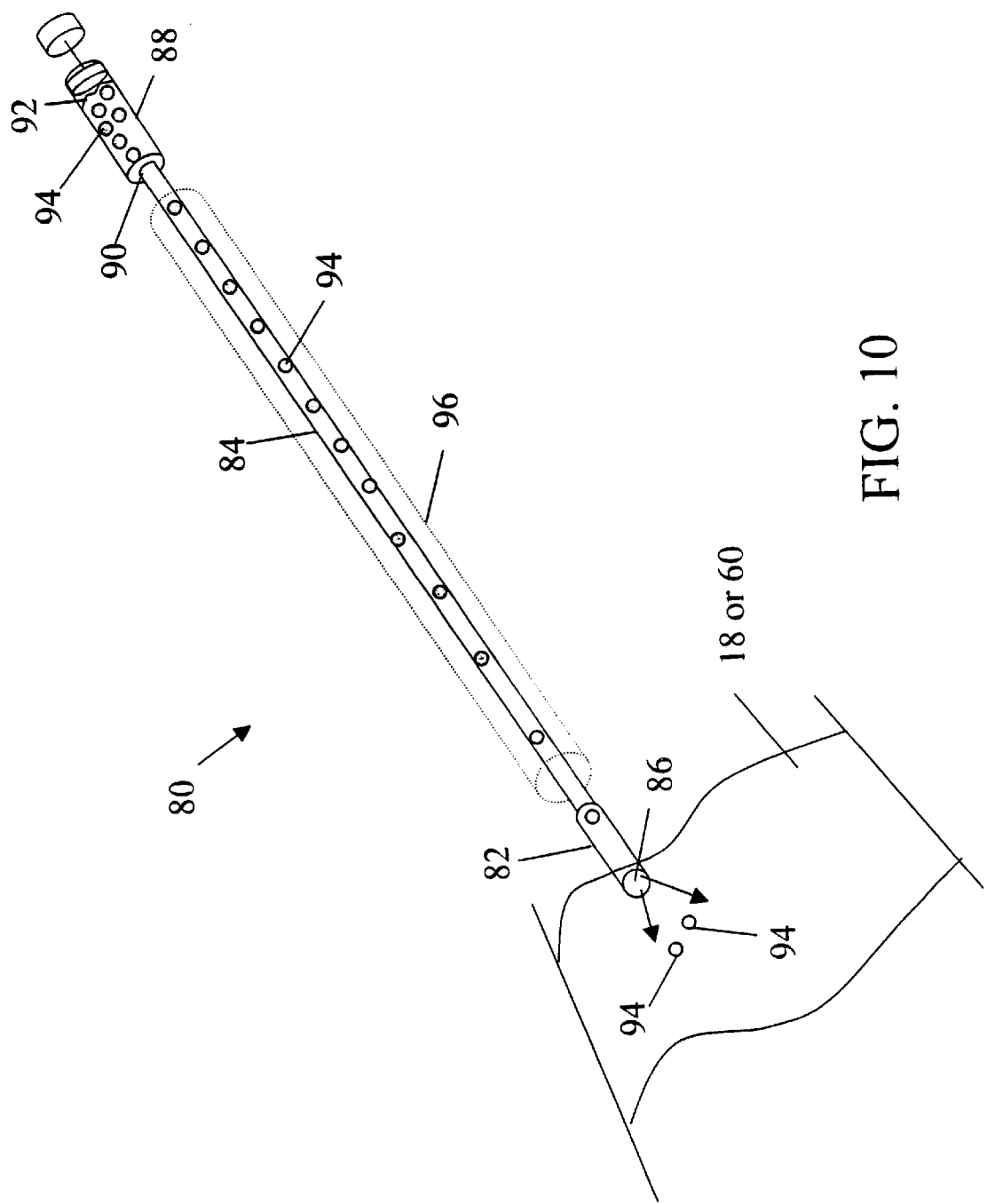
Fig. 10 is a perspective view showing the introduction of autogenous muscle grafts into the myocardium using an advanced muscle graft implantation system.
Figure 11:
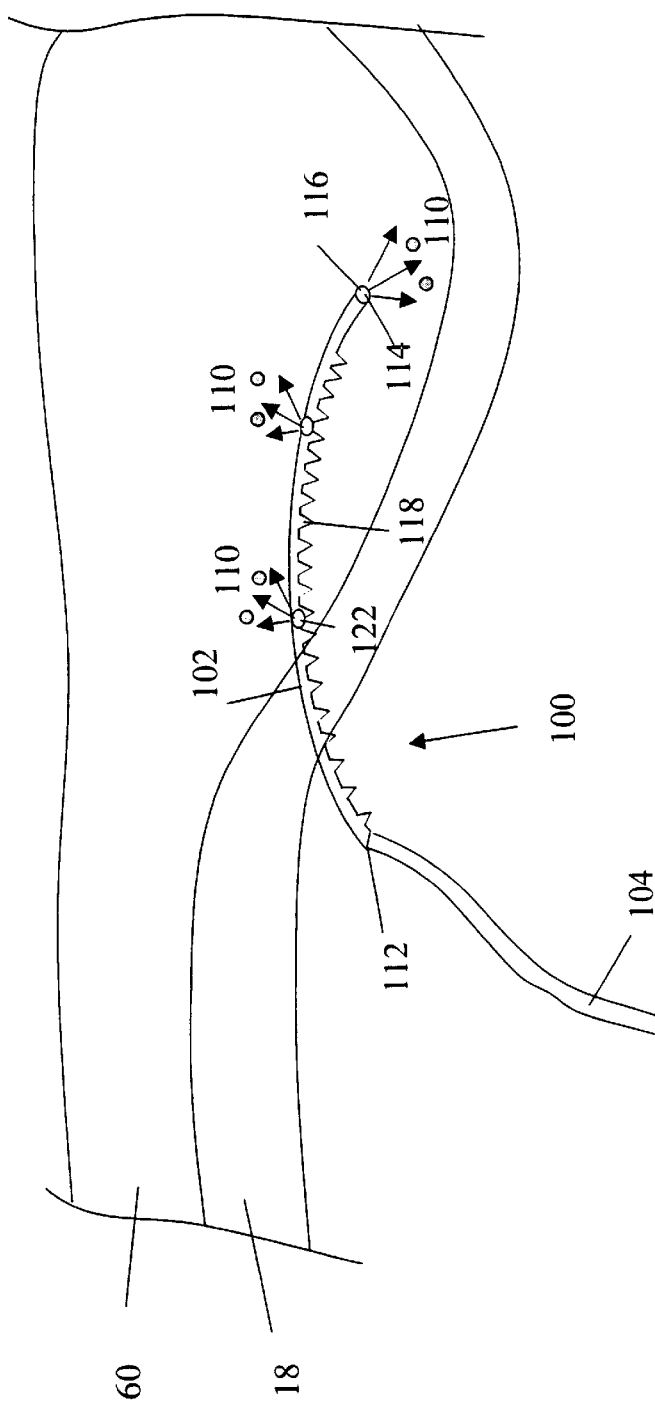
FIG. 11 is a perspective view showing the introduction of autogenous muscle grafts into the myocardium using an alternative advanced muscle graft implantation system.
Figure 12:
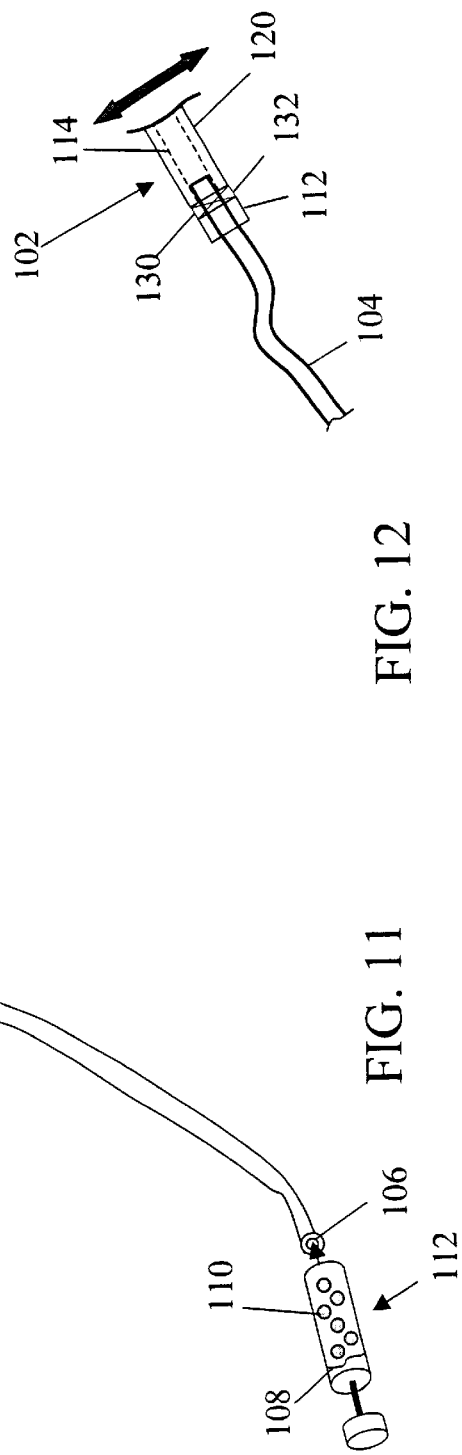
FIG. 12 is a fragmentary view showing a compliant feature of the implantation system of FIG. 11 that allows a muscle graft implantation instrument to be inserted into a beating myocardium.

Turning now to FIGS. 10–12, a modified muscle graft removal and attachment procedure may be used in which very small muscle grafts (e.g., cubes having side dimensions of not more than about 1–5 mm ) (hereinafter "micrografts") are removed as plugs or the like (not shown) from existing autogenous skeletal muscle tissue and implanted into the damaged area of the myocardium, or into the greater omentum. To facilitate implantation, the micro-grafts are placed in a saline solution (or other suitable liquid carrier) and delivered through an advanced muscle graft implantation system now to be described. In FIG. 10, a first micro-graft implantation system 80 is shown that includes a micro-graft implantation instrument 82 and a delivery tube 84. The implantation instrument 82 is mounted to a distal end of the delivery tube 84. Both the implantation instrument 82 and the delivery tube 84 are hollow and substantially rigid, being made from a material that is suitable for surgical use, such as stainless steel. The implantation instrument 82 has a sharpened distal tip 86 for cutting into tissue. The distal tip 86 is ported to allow egress of material from the instrument's hollow interior. A syringe 88 is attached to the proximal end 90 of the delivery tube 84. The syringe 88 carries a liquid carrier 92 having a plurality of micro-grafts 94 disbursed therein. With the syringe 88 attached to the delivery tube 84, the syringe plunger is depressed until the implantation instrument 82 and the delivery tube 84 are primed with the saline solution. Then the implantation instrument 82 and the delivery tube 84 are inserted through a thoracoscopy port 96 (shown in phantom) until the tip of the implantation instrument 82 penetrates the surface of either the myocardium 60 or the greater omentum 18. When the implantation device 82 is properly positioned, the syringe plunger is further depressed to implant the micro-grafts 94 into the receiving tissue. Moving the implantation instrument 92 from one location to the next, the implantation process is repeated as necessary until a suitable quantity of the micro-grafts 92 have been implanted. The greater omentum 18 is then attached to the myocardium 60 in the manner described above.

An alternative micro-graft implantation system 100 is shown in FIGS. 11 and 12.

In the system 100, an implantation instrument is formed as a hollow suturing needle 102, and a delivery tube is formed as a hollow suture 104. The suture 104 has a centrally disposed hollow interior passage 106, extending throughout its length, for delivering a saline solution (or the like) 108 containing micro-grafts 110 received from a syringe 112 or other source. The suture 104 can be made from any suitable flexible tubular or hollow string material, such as polyurethane, polypropylene, nylon or the like. The suture 104 can be smooth, as shown in FIG. 11, or it can have a roughened surface to stimulate blood flow in the tissue through which it passes, to thereby promote healing. Surface roughening can be provided in a variety of ways, such as by embedding nodules made from silicon or the like in the suture's outer surface. Alternatively, if the suture 104 is not too thick, it could be braided. However, because the suture 104 must have an inside diameter of sufficient size to permit passage of the micro-grafts 110, it will generally not be braided.

The suture 104 is connected to a suture attachment (base) end 112 of the suturing needle 102. The suturing needle 102 includes a centrally disposed hollow passage 114 extending throughout its length. Delivery of the micro-grafts 110 into the myocardium 60 or the greater omentum 18 is made at a pointed end 116 of the suturing needle 102, which is centrally vented by the hollow passage 114. Optionally, the suturing needle 102 may be formed with serrations 118 (or other surface roughening) along at least one side of an elongated intermediate section 120 thereof that extends between the two ends of the suturing needle. This helps to abrade the receiving tissue during suturing, thereby increasing blood flow to the affected area to promote healing. The intermediate section 120 may be laterally vented, as shown at 122, to provide additional pathways for the delivery of the micro-grafts 110 into the myocardium 60 or the greater omentum 18. To implant the micro-grafts 110, the suturing needle is introduced into the receiving tissue. Here the motion of the suturing needle is momentarily interrupted. With the suturing needle being primed with the micro-graft bearing saline solution 108, the plunger of the syringe 112 is depressed to implant the micro-grafts 110 through the opening 114 and/or the lateral vents 122. The suture is then completed in conventional fashion. It will be appreciated that although the suturing needle 102 is shown in FIG. 11 as being curved, it could also be straight.

Turning now to FIG. 12, the suturing needle 102 may optionally be formed with a compliant section 130 located at or near its base end 112. The compliant section 130 allows the intermediate section 120 to move laterally relative to the base end 112 such that the suturing needle 102 can be inserted into the beating myocardium 60, while being held by the base end, without laterally tearing the myocardial tissue. The compliant section 130 can be provided in many ways. For example, the compliant section 130 could be implemented as a flexible coupling 132 such as a spring, a rubber or plastic insert, or the like, disposed between the base end 112 and the intermediate section 120. A spring could also be combined with an insert. Alternatively, the compliant section 130 can be formed with the assistance of the suture 104. In this configuration (shown in FIG. 12), the suture 104 extends into the intermediate section 128 a sufficient distance to ensure proper attachment thereto. The fit should be tight enough to prevent detachment during the suturing procedure. The compliancy of the suture 104 will assist the flexible coupling 130 in facilitating movement of the suturing needle intermediate section 120 relative to the base end 112. If the suture 104 is stiff enough, the flexible coupling 132 could be implemented as a hinge having no bending resistance. Alternatively, no flexible coupling 132 may be required at all, such that the compliant section 130 is provided entirely by the suture 104 itself. During suturing, the suturing needle 102 can be held at the base end 124 while the pointed end 116 is inserted into the beating myocardium 60. By allowing the suturing needle 102 to flex about the compliant section 130, lateral tears and other unwanted tissue damage can be avoided.

Accordingly, a method of autogenous cell patch cardio myoplasty using noninvasive thoracoscopy has been disclosed. The treatment promises to significantly improve the long-term prognosis of patients with cardio myopathy. Indeed, post-healing analysis of animal test subjects that underwent the treatment yielded positive results in all areas of testing conducted. For example, angiography performed six weeks after treatment showed a good connection of blood vessels between the greater omentum and the myocardium. Esophageal echocardiography and electromyographic imaging revealed normal contraction of the ventricular wall with little or no hypokinesia, even in test subjects that received cardioarterial ligation during the procedure. Gross specimens of the heart obtained after six weeks of healing revealed marked adherence of the transplanted muscle and greater omentum to the myocardium. The histology of the transplanted muscle revealed significant muscle regeneration with migration into the ventricular wall, indicating good healing. Cell specimens of the transplanted muscle showed normal cytochrome oxidation activity and a gel eletrophoritic pattern of contractile protein, namely actin, that is similar to that of myocardial actin.

While various embodiments of the invention have been described, it should be apparent that many variations and alternative embodiments could be implemented in accordance with the invention. It is understood, therefore, that the invention is not to be in any way limited except in accordance with the spirit of the appended claims and their equivalents.

What is claimed is:

1. A method of autogenous cell patch cardio myoplasty using noninvasive thoracoscopy, comprising the steps of:
   (a) effecting separation between a greater omentum and either a greater curvature of a stomach or a transverse colon in a trans-abdominal cavity, such that said greater omentum has a free end and a base end attached to, and receiving a supply of blood from, either of said transverse colon or said stomach;
   (b) ligating blood vessels of said greater omentum as necessary at said greater omentum free end to permanently block blood flow from said blood vessels;
   (c) introducing said free end of said greater omentum into a left pleura cavity through an in a diaphragm separating said left pleural cavity from said trans-abdominal cavity;
   (d) removing muscle grafts from skeletal muscle tissue of said patient;
   (e) form an opening in a pericardium covering a heart in said left pleural cavity, said opening exposing a damaged area of a myocardium;
   (f) wrapping said free end of said greater omentum around said heart with said skeletal muscle grafts implanted in said greater omentum or said damaged myocardium area;
   (g) attaching said free end of said greater omentum to said heart to reinforce said muscle grafts and enrich them with blood flow from said greater omentum; and
   wherein step (f) includes implanting said muscle grafts to said free end of said greater omentum prior to wrapping said free end of said greater omentum around said heart.

2. A method of autogenous cell patch cardio myoplasty using noninvasive thoracosceopy, comprising the steps of:
   (a) effecting separation between a greater omentum and either a greater curvature of a stomach or a transverse colon in a trans-abdominal cavity, such that said greater omentum has a free end and a base end attached to, and receiving a supply of blood from, either of said transverse colon or said stomach;
   (b) ligating blood vessels of said greater omentum as necessary at said greater omentum free end to permanently block blood flow from said blood vessels;
   (c) introducing said free end of said greater omentum into a left pleural cavity through an opening in a diaphragm separating said left pleural cavity from said trans-abdominal cavity;
   (d) removing muscle grafts from skeletal muscle tissue of said patient;
   (e) forming an opening in a pericardium covering a heart in said left pleural cavity, said opening exposing a damaged area of a myocardium;
   (f) wrapping said free end of said greater omentum around said heart with said skeletal muscle grafts implanted in said greater omentum or said damaged myocardium area;
   (g) attaching said free end of said greater omentum to said heart to reinforce said muscle grafts and enrich them with blood flow from said greater omentum;
   wherein steps (d) and (f) include retrieving said muscle grafts as small plugs from said patient's skeletal muscle tissue and implanting said grafts into said damaged myocardium area or said greater omentum using a muscle graft implantation system; and
   wherein said implantation system includes a muscle graft implantation instrument mounted to a distal end of a delivery tube, and a source if a muscle graft containing liquid carrier connected to a proximal end of said delivery tube.

3. A method in accordance with claim 2, wherein said muscle graft implantation instrument is a hollow suturing needle having one or more muscle graft delivery openings therein, and wherein said delivery tube is a hollow suture.

4. A method in accordance with claim 2, further including a step (h) of forming a pocket in said greater omentum and inserting a drug or medicine delivery vehicle therein.

5. A method of autogenous cell patch cardio myoplasty using noninvasive thoracoscopy, comprising the steps of:
   (a) effecting separation between a greater omentum and either a greater curvature of a stomach or a transverse colon in a trans-abdominal cavity, such that said greater omentum has a free end and a base end attached to, and receiving a supply of blood from, either of said transverse colon or said stomach;
   (b) ligating blood vessels of said greater omentum as necessary at said greater omentum free end to permanently block blood flow from said blood vessels;
   (c) introducing said free end of said greater omentum into a left pleural cavity through an opening in a diaphragm separating said left pleural cavity from said trans-abdominal cavity;
   (d) removing muscle grafts from skeletal muscle tissue of said patient;
   (e) forming an opening in a pericardium covering a heart in said left pleural cavity, said opening exposing a damaged area of a myocardium;
   (f) wrapping said free end of said greater omentum around said heart with said skeletal muscle grafts implanted in said greater omentum or said damaged myocardium area, said implantation being performed by a muscle graft implantation system that implants said muscle grafts as muscle graft plugs carried in a liquid medium; and
   (g) attaching said free end of said greater omentum to said heart to reinforce said muscle grafts and enrich them with blood flow from said greater omentum.

6. A method in accordance with claim 5, wherein said implantation system comprises a reservoir containing a supply of said muscle graft plugs in said liquid medium, said reservoir having means for evacuating said reservoir, said implantation system further including an elongated delivery system.

7. A method in accordance with claim 6, wherein said elongated delivery system comprises a delivery tube disposed within a thoracoscopy port and a sharpened distal tip.

8. A method in accordance with claim 7, wherein said elongated delivery system comprises a hollow suture and a hollow suturing needle with one or more delivery openings therein.

9. A method in accordance with claim 8, wherein said suture comprises a roughened surface.

10. A method in accordance with claim 8, wherein said suturing needle comprises serrations.

11. A method in accordance with claim 8, wherein said suturing needle comprises a compliant section proximate a base end thereof.

* * * * *